United States Patent [19]
Rzeszotarski et al.

[11] Patent Number: 4,761,405
[45] Date of Patent: Aug. 2, 1988

[54] ANTAGONISTS OF SPECIFIC EXCITATORY AMINO ACID NEUROTRANSMITTER RECEPTORS HAVING INCREASED POTENCY

[75] Inventors: Waclaw J. Rzeszotarski, Millersville; Donald J. Kyle, Baltimore, both of Md.

[73] Assignee: Nova Pharmaceutical Corporation, Baltimore, Md.

[21] Appl. No.: 21,703

[22] Filed: Mar. 4, 1987

[51] Int. Cl.$^4$ .................. C07F 9/38; A61K 31/13; A61K 31/195; A61K 31/045
[52] U.S. Cl. .................. 514/114; 260/502.5 G; 514/112; 558/190; 558/192
[58] Field of Search ............. 260/502.5 G; 514/112, 514/114, 120, 190, 192

[56] References Cited
U.S. PATENT DOCUMENTS

| 4,147,780 | 4/1979 | Dingwall et al. | 260/502.5 G |
| 4,477,391 | 10/1984 | Collins | 260/502.5 G |
| 4,483,853 | 11/1984 | Collins et al. | 260/502.5 G |
| 4,656,298 | 4/1987 | Dingwall et al. | 514/114 |
| 4,657,899 | 4/1987 | Rzeszotarski et al. | 514/114 |

OTHER PUBLICATIONS
Matoba et al., Chem. Pharm. Bull., vol. 32, No. 10, 1984, pp. 3918–3925.

Primary Examiner—J. E. Evans
Attorney, Agent, or Firm—Breneman & Georges

[57] ABSTRACT

The invention pertains to novel, potent anticonvulsants, analgesics, cognition enhancers and neuroprotectants achieving their action through the antagonism of specific excitatory amino acid neurotransmitter receptors. In particular, the invention is directed to ω-[2-(phosphonoalkylenyl)-cycloalkyl]-2-aminoalkanoic acids having general formula:

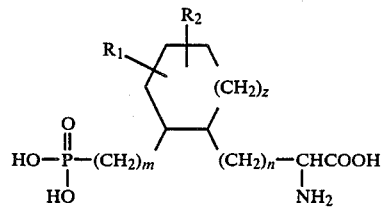

wherein $R_1$ and $R_2$ are the same or different and are selected from the group consisting of hydrogen, lower alkyl ($C_1$ to $C_6$), alkyl ($C_7$ to $C_{12}$), fatty acid chain ($C_{13}$ to $C_{24}$), aryl, aralkyl, hydroxyl; the stereoisomers being in their resolved or racemic form; n and m=0,1,2 or 3; z=0,1 or 2; the cycloalkyl ring being replaced with the cycloalkenyl ring; and the pharmaceutically acceptable salts and derivatives thereof.

15 Claims, No Drawings

ANTAGONISTS OF SPECIFIC EXCITATORY AMINO ACID NEUROTRANSMITTER RECEPTORS HAVING INCREASED POTENCY

BACKGROUND OF THE INVENTION

1. Field of the Invention

The present invention pertains to novel, potent anticonvulsants, antiepileptics, analgesics and cognition enhancers achieving their action through the antagonism of specific excitatory amino acid (EAA) neurotransmitter receptors. In particular, the invention is directed to ω-[2-(phosphonoalkylenyl)cycloalkyl]-2-aminoalkanoic acids, their pharmaceutically acceptable salts and derivatives, and to the methods of synthesizing the same.

2. Description of the Prior Art

While L-glutamate and L-aspartate were initially thought merely to participate in brain metabolism, sufficient molecular pharmacological, biochemical and electrophysiological evidence now exists to suggest that these amino acids are neuroexcitatory transmitters [D. R. Curtis, A. W. Duggar, D. Felix, G. A. R. Johnston, A. K. Tebecis and J. C. Watkins. Brian Res., 41, 283–301 (1972)].

For many years following the initial characterization of the neuro-excitotoxic actions of amino acids, it was tacitly assumed that all compounds of this type (agonists and antagonists) acted upon the same receptor. The discovery of relatively selective antagonists of different actions of EAAs or of actions of different EAA compounds, has changed this perception, and it is now accepted that multiple recognition sites for EAAs are present in the vertebrate central nervous system[J. C. Watkins and R. H. Evans. Ann. Rev. Pharmacol. Toxicol., 21, 165–204 (1981)]. Defined by prototypical agonists or antagonists, these include:

1. receptors activated by L-glutamate (Glu) and the conformationally restricted Glu analog, quisqualic acid (Quis), and antagonized selectively by glutamic acid diethylester, 2. receptors responsive to the synthetic analogue of L-aspartate (Asp), N-methyl-D-aspartate (NMDA), the isoxazole neurotoxin, quniolinic acid (Quin) and, probably, to Asp itself. These receptors are antagonized by D-(−)-2-amino-5 phosphonopentanoic acid (AP5), D(−)-2-amini-7-phosphonoheptanoic acid (AP7), and the divalent cation, $Mg^{++}$, 3. receptors activated by the pyrrolidine neuroexcitotoxin, kainic acid (KA), for which no specific antagonists have yet been identified and, 4. receptors antagonized by L-(+)-2-amino-4-phosphonobutyric acid (LAP4). Originally indentified as an EAA antagonist by electrophysiological means, LAP4 inhibits the response at the lateral perforant pathway synapses of the hippocampus to an unidentified endogenous excitatory substance. The possibility that Glu is this neurotransmitter is minimal and recent evidence suggests that the N-blocked dipeptide, N-acetylaspartyl-L-glutamate may function in this capacity [J. M. H.ff-French-mullen, K. J. Koller, R. Zaczek, Li Hori, J. T. Coyle and D. O. Carpenter. Proc. Natl. Acad. Sci. U.S.A., 82, 3897–4001 (1985)].

Beyond these fundamental receptor categories, it has become increasingly apparent that subdivisions may exist within each receptor category. For example, receptors for NMDA appear to be pharmacologically distinct in different regions of the brain [T. W. Stone and J. H. Connick, Neuroscience, 15, 597–617 (1985)] and one subpopulation of NMDA receptors may be allosterically linked to the site of action of the dissociative anesthetics, phencyclidine and certain benz(-F)isoquinolines. The novel tricyclic anticonvulsant MK801 may effect its primary action via an allosteric modulation of NMDA receptors [H. F. Wong et al. Proc. Natl. Acad. Sci. U.S.A., 83, 7104–7108 (1986)].

EAA's possibly acting through one or more of these receptors, have been implicated in the etiology of various pathological conditions affecting the CNS. Thus, KA [K. Biziere, J. T. Slevin, R. Zaczek, J. F. Collins and J. T. Coyle. In: *Advances In Pharmacology and Therapeutics:* H. Yoshida, Y. Hagihara and S. Ebashi, eds.; Pergamon, New York, 1982; pp 271–276], NMDA [R.Zaczek, J. Collins and J. T. Coyle. Neurosci, Letts., 24, 181–186 (1981)] and the endogenous EAA, Quin [R. Schwarcz, W. O. Whetsell and R. M. Mango. Science, 219, 316–318 (1983)], have been used to produce in animals a syndrome analogous to human epilepsy; the anatomical and neurochemical lesions and deficiencies produced by these compounds in animals are similar to the characteristics seen postmortem in the brains of patients dying with Huntington's disease [J. Coyle, and R. Schwarcz. Nature, 263, 244–246 (1976)] and epilepsy. Kainate administration can produce a limbic structure lesion that mimicks Ammon's Horn Sclerosis, an abnormality frequently found in temporal lobe epilepsy. Research on this model of temporal lobe epilepsy has suggested the endogenous EAA's may play a role in this disorder that is particularly resistant to existing antiepileptics [J. V. Nadler, B. W. Perry, C. W. Cotman. Nature, 271, 676–677 (1981)]. In addition to Huntington's disease and epilepsy, it has been suggested that EAA's may contribute to ALzheimer's disease [A. C. Foster, J. F. Collins and R. Schwarcz. Neuropharmacology, 22, 331–1341 (1983)], E. Roberts. In: *Strategies for the development of an Effective Treatment of Senile Dementia:* (E. Crook and L. Gershon, eds.; Mark Power Assoc: New Camarin, Conn. 1981; pp 247–230], the neuronal death following stroke and other instances of cerebral ischemia, [R. P. Simon, J. H. Swan, T. Griffiths and B. S. Meldrum. Science, 226, 850–852 (1984): S. Rothman. J. Neuroscience, 4, 1884–1891 (1984)] and hereditary olivopontocerebellar atrophy [J. T. Coyle, TINS, 5, 287–288 (1982)]. Additionally, the growing recognition of an association between NMDA receptors and the dissociative anesthetics which are functional antagonists of NMDA suggests that NMDA receptor antagonists may elicit antinociceptive responses. Should this be substantiated, such compounds would represent an entirely novel category of analgesics since unlike currently available drugs which are universally receptor agonists, the analgesic properties of compounds acting at NMDA receptors would be elicited through receptor blockade.

Because of the conceptual link between EAAs activity at specific brain receptors in vivo, excitotoxic lesions caused by EAA in animals, the pathogenesis of the above neurodegenerative diseases including the dementias, and the the potential application of EAA antagonists for uses such as antinociception, it is logical to explore pharmacologic means to antagonize endogenous excitatory and/or excitotoxic neurotransmitters. The development of antagonists of exogenous excitotoxins such as KA is also logical, since there is presumably and yet undiscovered specific endogenous substance that acts at brain KA receptors. The advent of potent and selective antagonists of EAA's exemplified by α-amino-ω-phosphonoalkylenylcarboxylic acids (the most potent and selective being D(−)2-amino-7-phosphonoheptanoic acid, D(−)AP7) has provided a point of departure for the pharmacologic intervention of EAA action at their receptors.

Besides interferring with the neurotoxic and convulsive actions of NMDA, the exogenous excitotoxin, IBO, and the endogenous excitotoxin Quin (but not KA) [A. C. Foster, J.F. Collins and R. Schwarcz. Neuropharmacology, 22, 1331-1341 (1983): R. Schwarcz, F.J. Collins and D. A. Parks. Neurosci. Letts., 33, 85-90 (1982)], AP7 (i.c.v. and i.v.) protects against audiogenically-induced seizures in genetically susceptible mice [M. J. Croucher, J. F. Collins and B. S. Meldrum. Science, 216, 899-901 (1982)]. I.v. AP7 suppresses photically-induced myoclonus in the baboon [B. S. Meldrum, M. J. Croucher, G. Badman and J. F. Collins. Neurosi. Letts., 39, 101-104 (1983)], increased threshold current for electroshock-induced seizures of mice and prevents chemically-induced seizures in rodents [S. J. Czuczwar and G. Meldrum. Eur. J. Pharmacology, 83, 335-338 (1982)]. Very recently, AP7 (intrahippocampally) has been reported to markedly reduce or eliminate ischemic brain damage in the rodent carotid artery occlusion model of stroke [R. P. Simon, J. H. Swan, T. Griffiths and B. S. Meldrum. Science, 226, 850-852 (1984)], and another, less potent, EAA antagonist δ-D-glutamyl glycine, has been shown to protect cultured rat hippocampal neurones from degeneration under conditions of oxygen depletion while blocking the toxicity of exogenously applied Glu and Asp [S. Rothman. J. Neuroscience, 4, 1884-1891 (1984)]. Mixed KA and Quis receptor antagonists have also been shown to possess anticonvulsant activity [M. J. Croucher, B. S. Meldrum, A. W. Jones and J. C. Watkins. Brain Res., 377, 111-114 (1984)]. Finally, and significantly, several lines of circumstantial evidence link EAAs, especially Glu, with the onset of age-associated neurodegenerative diseases, including Alzheimer's disease [J. T. Greenamyre, J. B. Penney, A. B. Yound, C. D'Amato, S. P. Hicks, I. Schoulson. Science, 227, 1496-1498 (1985)], and with tardive dyskinesia [J. W. Olney. In: *Excitotoxins* K. Fuxe, R. Roberts, and R. Schwarcz, eds].

SUMMARY OF THE INVENTION

The present invention provides a potent, selective EAA neurotransmitter receptor antagonist having the general formula:

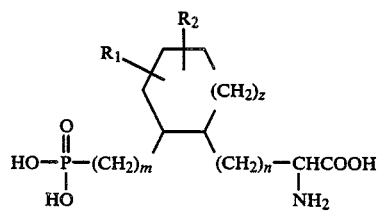

wherein $R_1$ and $R_2$ are the same or different and are selected from the group consisting of hydrogen, lower alkyl [$C_1$ to $C_6$], alkyl [$C_7$ to $C_{12}$], fatty acid chain [$C_{13}$ to $C_{24}$], aryl, aralkyl, hydroxyl, and the derivatives thereof; the stereoisomers being in their resolved or racemic form; n and m=0, 1, 2, or 3; z=0, 1 or 2; the cycloalkyl ring being replaced with the cycloalkenyl ring; and the pharmaceutically acceptable salts and derivatives thereof.

DETAILED DESCRIPTION OF THE INVENTION

The structure and formulation of the novel compounds of the invention was the result of the extensive research investigation into the antagonism of heterogenic EAA neurotransmitter receptors.

Defined by prototypical agonsits or antagonistis, these include:

1. receptors activated by L-glutamate (Glu) and the conformationally restricted Glu analog, quisqualic acid (Quis), and antagonized selectively by glutamic acid diethylester, 2. receptors responsive to the synthetic analogs of L-aspartate (Asp), N-methyl-D-aspartate (NMDA), the isoxazole neurotoxin, ibotenic acid (Ibo), the pyridinedicarboxylic acid neurotoxin, quinolinic acid (Quin) and, probably, to Asp itself. These receptors are antagonized by D(−)-2-amino-5-phosphonopentanoic acid (AP5), D(-)2-amino-7-phosphonoheptanoic acid (AP7), and the divalent cation, $Mg^{++}$, 3. receptors activated by the pyrrolidine neuroexcitotoxin, kainic acid (KA), for which no specific antagonists have yet been identified and, 4. receptors antagonized by L(+)-2-amino-4-phosphonobutyric acid (LAP4). Originally identified as an EAA antagonists by electrophysiological means, LAP4 inhibits the response at the lateral perforant pathway synapses of the hippocampus to an unidentified endogenous excitatory substance. The possibility that Glu is this neurotransmitter is minimal and recent evidence suggests that the N-blocked dipeptide, N-acetylaspartyl-L-glutamate may function in this capacity [J. M. H. ff-French-mullen, K. J. Koller, R. Zaczek, Li Hori, J. T. Coyle and D. O. Carpenter. Proc. Natl. Acad. Sci. U.S.A., 82, 3897-4000 (1985)].

The structure of novel compounds provides potent antagonist having greater affinity toward one of the receptors or no affinity to some of them rendering the compound selective. This would therefore permit one to selectively antagonize one EAA receptor in the tissues also containing other EAA receptors. As a result of the greater affinity and selectivity of the present invention fewer side effects are exhibited by the novel compounds.

The high affinity and selectivity of such compounds (e.g. 3-(2-phosphonoethyl)cyclohexyl-2-aminopropionic acid or 4-(2-phosphonomethyl)cyclohexyl-2-aminobutyric acid) have been demonstrated in receptor binding studies and in mice by their ability to provide protection in pentylenetetrazol (PTZ) induced seizures.

The novel compounds of the invention can be readily prepared by the following synthetic route:

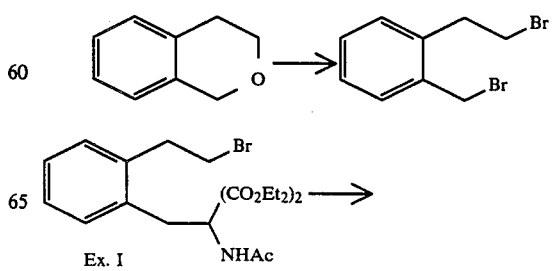

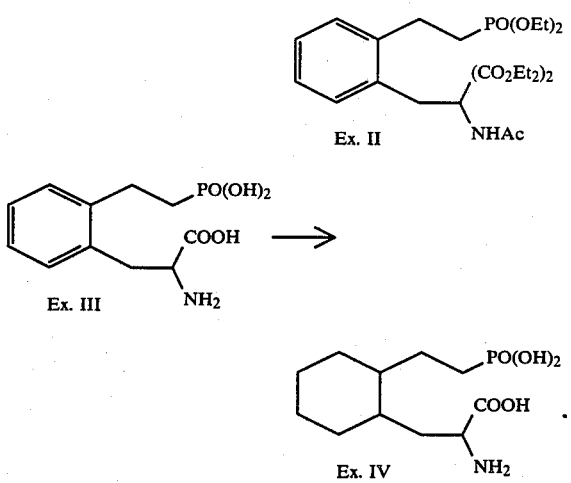

In the route leading to compounds of examples I to IV, the reaction of isochroman with a solution of hydrobromic and acetic acids in a sealed tube gives the required intermediate o-(2-bromoethyl)-benzyl bromide in high yield [E. L. Anderson; F. G. Holliman. *J. Chem Soc.*, 1037,(1950)]. Reacting the intermediate o-(2-bromoethyl)benzyl bromie with the sodium salt of diethyl acetamidomalonate gives the compound of example I. Reaction of this compound with triethylphosphite gives the compound of example II in 75% yield. Hydrolysis in 6N HCl gives the compound of example III. The hydrogenation of the compound example III in a bomb hydrogenator in the presence of ruthenium dioxide catalyst leads to the compound of example IV.

The preparation of compounds for administration in pharmaceutical preparations may be in a variety of well known methods known to those skilled in the art of pharmacy. More specifically the novel compounds may be formulated as an acid, (e.g., HCl salt), sulfate, phosphate, nitrate, methanesulfonate, tartrate or a base salt and other pharmaceutically acceptable salts and compositions.

In parenteral administration of the novel compounds and compositions of the invention the compounds may be presented in aqueous injection solutions which may contain antioxidants, buffers, bacteriostats, etc. Extemporaneous injection solutions may be prepared from sterile pills, granules or tablets which may contain diluents, dispersing and surface active agents, binders and lubricants.

In the case of oral administration, fine powders or granules of the compound may be formulated with diluents and dispersing and surface active agents, and may be prepared in a draft in water or in a syrup, in capsules or cachets in the dry state or in a non-aqueous suspension, when a suspending agent may be included. The compounds may also be administered in tablet form along with optional binders and lubricants, or in a suspension in water or a syrup or an oil or in a water/oil emulsion and may include flavoring, preserving, suspending, thickening and emulsifying agents. The granules or tablets for oral administration may be coated and other pharmaceutically acceptable agents and formulations may be utilized as known to those skilled in the art.

The following examples are illustrative of compounds of the invention but are not to be construed as limiting the invention thereto.

EXAMPLE I

Ethyl 3-[2-(2-bromoethyl)phenyl]-2-acetamido-2-carboethoxypropanoate

To a solution of 0.41 g (18 mmol) Na in 100 mL of dry ethanol was added portionwise 3.9 g (18 mmol) of solid diethylacetamidomalonate. This mixture was stirred at reflux under nitrogen for 2 h then cooled to 0°–10° C. then stored 24 h at room temperature. The precipitated inorganic salt was removed by filtration and discarded. The solvent was removed under reduced pressure yielding a golden oil. This oil was chromatographed on a reverse phase column (C-18) with methanol-water (1:1) as eluent. The combined fractions were concentrated under reduced pressure to yield 5.6 g (75%) of the product as a white solid, mp 86.0°–86.5° C. IR(nujol): 1785, 1637 cm$^{-1}$. $^1$H NMR(CDCl$_3$) $\delta$1.2(t,6H); 1.9 (s,3H); 2.8–3.5 (m,4H), 3.6 (5,2H); 4.2 (q,4H); 6.8 (s,1H); 7.2 (m,4H). Anal. Calcd. for C$_{18}$H$_{24}$NO$_5$Br: C,52.18; H,5.84; N,3.38. Found: C, 52.26; H, 5.86; N, 3.34.

EXAMPLE II

Ethyl 3-[2-(2-diethylphosphonethyl)phenyl]-2-acetamido-2-carboethoxypropanoate

A solution of 0.5 g (1.2 mmol) of ethyl 3-[2-(2-bromoethyl)phenyl]-2-acetamido-2-carboethoxypropanoate in 10 mL of P(OEt)$_3$ was stirred at reflux for 4 h. The excess P(OEt)$_3$ and the volatile by-products were removed from the mixture by distillation under vacuum. The remaining viscous oil was initially purified by column chromatography (C-18,MeOH:H$_2$O;4:1), then by preparative HPLC (C-18, MeOH:H$_2$O, 7:3) giving 0.48 g (86%) of the product as a clear viscous oil. IR(Nujol) 1745.9, 1676.5 cm$^-$. $^1$H NMR (CDCl$_3$) $\delta$1.2 (t,6H); 1.9 (s,3HO;2.8–3.5 (m,4H), 3.6 (5,2H); 4.2 (q,4H); 6.8 (s,1H); 7.2 (m,4Hl). Anal. Calcd. For C$_{18}$H$_{24}$NO$_5$Br: C, 52.18; H, 5.84; N,3.38. Found: C, 52.26; H, 5.86; N, 3.34.

EXAMPLE III

2-Amino-4,5-benzo-7-phosphonoheptanoic acid

A solution of 7.9 g (16.8 mmol) of the 3-[2-(2-diethylphosphonoethyl)-phenyl]-2-acetamido-2-carboethoxypropanoate in 40 mL of 6N HCl was stirred at vigorous reflux for 14 h. After cooling to room temperature the reaction mixture was concentrated at reduced pressure yielding an oil. This oil was washed with four 25 mL portions of water then dissolved in 20 mL 95% ethanol and propylene oxide added dropwise. The precipitated crude acid was collected by filtration. Recrystallizaton from dilute ethanol yielded 4.1 g (90%) as a white solid, mp 241°–244° C. IR(Nujol): 1712 cm $^{-1}$. $^1$H NMR (D$_2$O) $\delta$1.5–2.2 (m,2H); 2.6–3.3 (m,4H); 3.9–4.2 (t,1H); 7.2 (m,4H). Anal. Calcd. for C$_{11}$H$_{16}$NO$_5$P: C, 48.35; H, 5.90; N, 5.13. Found: C, 48.69; H, 6.16; N, 4.95.

EXAMPLE IV 2-amino-4.5-(1,2-cyclohexyl)-7-phosphonoheptanoic acid 2-amino-4,5-benzo-7-phosphonoheptanoic acid(2.0 g; 7.3 mmol) was placed in a one liter bomb hydrogenator with 2.4 g RuO$_2$ in 650 mL of a 2:1 water/ethanol mixture. Following evacuation of air, the reactor was filled with H$_2$ to a pressure of 1350 psi. The reactor was then heated to 100° C. at which point the pressure was 1800 psi. After stirring rapidly for 7 days, the container was cooled and the solution filtered twice through celite. After complete removal of solvents, a white solid was collected. This was recrystallized from hot water giving essentially pure product (1.83 g; 90%). The material was collected by suction filtration and had a melting point of 144°–146° C. $^1$H NMR (CDCl$_3$): δ3.8(m,2H); 3.5(dd,1H), 1-2(mult,14H). TLC (AvicelF): One spot of R$_f$=0.75; 2:1 Water/MeOH. IR(KBr): 3615–2278, 1630, 1535, 1455, 1121, 1051, 928 cm$^{-1}$. Anal. Calcd. for C$_{11}$H$_{22}$NO$_5$P: C, 47.31; H, 7.94; N, 5.01. Found: C, 47.4; H, 8.08; N, 5.00.

EXAMPLE V

In vitro Receptor Binding Assays

The potency of the compound described in example IV to inhibit the specific binding of various EAA ligands to rat forebrain membranes was examined using standard in vitro binding techniques. Specifically, example IV was evaluated for potency to inhibit the specific binding of [$^3$H]kainic acid ([$^3$H]KA),[$^3$H]RS-α-amino-3-hydroxy-5-methyl-4-isoxazole propionic acid([$^3$H]AMPA) and [$^3$H]3-(2-carboxypiperazin-4-yl) propyl-1-phosphonic acid([$^3$H]CPP) to KA, QUIS and NMDA receptors, respectively.

Methods were as follows: rat forebrain membranes were prepared as described by Enna and Synder [Mol. Pharmacology, 13, 422–453 (1977)] and the "buffy coat" preparation was washed three additional times by centrifugation (45,000 g; 10 min; 4° C.) with intermittent resuspensions (20 vol; w/v) in fresh buffer (Tris HCl; 0.05M; pH 7.4; 23° C.). Following the final wash, pellets were stored frozen (−20° C.) until used.

On the day of assay, pellets were thawed to room temperature, resuspended in buffer (Tris HCl; 0.05 M; various pH; 23° C.) and washed three additional times by centrifugation as described in the preceeding paragraph. For assay, the washed tissue was resuspended in buffer at a concentration of 10 mg/mL. All procedures were performed using triplicate incubations in a final volume of 2 mL which consisted of the tissue suspension (1 mL), ligand, the compound(s) of interest and 1 mL of buffer. In every instance, Glu (10$^{-3}$M) was used to determine nonspecific binding. Assays were terminated by centrifugation (45,000 g; 10 min; 4° C.), the pellet was washed rapidly and superficially with 2×2.5 mL of ice-cold buffer and dissolved in 1 mL of Protosol ® (New England Nuclear, Boston, Mass.). Following the addition of 6 mL of Econfluor ® (New England Nuclear, Boston, Mass.) radioactivity was determined using conventional liquid scintillation spectrophotometry.

Specific [$^3$H]AMPA (S.A.=27.5 Ci/mmol, New England Nuclear, Boston, Mass.) binding was examined according to the method of Murphy et al., [(Soc. Neurosci. Abs., 11, 109, (1985)] using Tris HCl buffer (pH 6.9) supplemented with 100 mM KSCN. Incubations were conducted for 60 min at 4° C. using a final ligand concentration of 4 nM.

Specific binding of [$^3$H]KA (S.A.=60 Ci/mmol, New England Nuclear, Boston, Mass.) was examined according to the method of London and Coyl [(Mol. Pharmacol., 15, 492–505 (1979)] using Tris HCl buffer (pH 7.4). Incubations were conducted for 90 min at 2° C. using a final ligand concentration of 2 nM.

Specific binding of [3H]CPP (S.A.=27 Ci/mmol, New England Nuclear, Boston, Mass.) was examined using a modification of the method of Murphy et al., [(J. Pharmacol. Exp. therap., (in press)] using Tris HCl buffer (pH 7.4). Incubations were conducted for 30 min at 23° C. using a final ligand concentration of 8 nM.

All assays were performed on three separate occassions. Appropriate reference compounds were evaluated in each assay and experiment using parallel incubations. All compounds were examined at a single concentration (50 uM) and activity was expressed as the percent inhibition of specific binding of each ligand.

Results are shown in Table 1. As expected, the order of potency of reference compounds to inhibit specific [$^3$H]KA binding to KA receptors was KA≦Glu>AMPA>>D(−)AP5=D(−)AP7=NMDA. Of the compounds tested, example IV was the least active to inhibit binding in this assay. Using [$^3$H]AMPA as a ligand, both Glu and AMPA were observed to be the most potent inhibitors of binding whereas KA showed moderate activity. The remaining reference compounds and example IV were without appreciable activity to inhibit the binding of the specific binding of [$^3$H]AMPA to Quis-type recognition sites in brain. Using [$^3$H]CPP to label NMDA-like sites, the order of potency of tested compounds to inhibit binding was D(−)AP5=D(−)AP7=Glu=NMDA>example IV. Both KA and AMPA were without appreciable activity in the [$^3$H]CPP assay. The results demonstrate the specificity of the various methods to label subtypes of EAA receptors in brain using in vitro ligand binding procedures. Furthermore, the data suggest the example IV interacts, albeit with moderate affinity, in a highly specific manner with NMDA-type receptors. Notably, the presence of multiple enantiomers of example IV in the NMDA receptor binding assay can be evoked to explain the moderate potency of the example to inhibit [$^3$H]CPP binding. For example, it is well established that only the D(−) isomers of the α-amino-ω-phosphonocarboxylic acids are active in this regard.

TABLE 1

POTENCY OF THE EXAMPLE COMPOUND AND VARIOUS REFERENCE COMPOUNDS TO INHIBIT SPECIFIC [$^3$H]LIGAND BINDING TO EXCITATORY AMINO ACID RECEPTORS IN BRAIN

| COMPOUND | PERCENT INHIBITION OF SPECIFIC LIGAND BINDING | | |
|---|---|---|---|
| | [$^3$H]CPP | [$^3$H]AMPA | [$^3$H]KA |
| GLU | 87 ± 8 | 95 ± 4 | 95 ± 3 |
| D(−)AP7 | 100 ± 0 | 7 ± 5 | 17 ± 2 |
| D(−)AP5 | 95 ± 4 | 3 ± 2 | 22 ± 1 |
| NMDA | 90 ± 5 | 5 ± 3 | 19 ± 5 |
| EXAMPLE IV | 33 ± 9 | 1 ± 1 | 9 ± 4 |
| AMPA | 7 ± 4 | 100 ± 0 | 64 ± 4 |
| KA | 3 ± 2 | 56 ± 5 | 100 ± 0 |

Method(s) have been described in the text. Values shown are the means ±S.E.M. of three separate determinations performed using triplicate incubations and are expressed as the percent inhibition of specifically bound ligand. All drugs were tested at a single concentration of 50 μM.

EXAMPLE VI

Protection Against Pentylenetetrazol (PTZ) - Induced Seizures

The anticonvulsant properties of example IV and of the reference compound DL(±)AP7 against seizures induced by subcutaneous (s.c.) injection of pentylenetetrazol (PTZ) were evaluated using mice.

For testing, PTZ was dissolved in saline (0.9%; w/v) and administered to male CF-1 mice (Charles Rivers: 20–25 g) at a dose of 90 mg/kg (s.c.) fifteen minutes (ICV) or thirty minutes (IP) after the administration of the test compounds. Example IV and the reference compound were dissolved in sline and administered in a final volume of 5 μL (ICV) or 200 μL (IP). Mice were observed for a period of thirty minutes following the administration of PTZ and seizures were scored as present or absent. Presence of seizures was defined as one or more episodes of clonic activity having a duration of five seconds or greater. Following preliminary dose-ranging studies, dose-response curves were generated using at least five different doses of each compound with eight animals at each dose. The dose of drug required to protect fifty percent ($ED_{50}$) of the test animals from PTZ-induced seizures was calculated using log-logit analysis. Ninety-five percent confidence intervals ($CL_{95}$) were calculated using the method of Litchfield and Wilcoxon [J. Pharmacol. Exp. Therap., 96, 99–113 (1949)].

Results are shown in Table 2. The $ED_{50}$ of DL(±)AP7 to attenuate PTZ-induced seizure activity was 1.37 μg ($CL_{95}$=0.45–4.1 μg) following ICV administration and in three separate experiments, varied from 176–199 mg/kg (low/high values) following IP administration. Example IV was 30–40-fold more potent than DL(±)AP7 to prevent PTZ-induced seizures following ICV administration and approximately 2-fold more potent (Table 2) than DL(±)AP7 to prevent seizures when administered IP. Thus, example IV represents a potent, novel and systemically active anticonvulsant agent in the PTZ seizure model of epilepsy.

EXAMPLE VII

Protection Against Maximal Electroshock (MES)-induced Seizures

The anticonvulsant properties of example IV and of the reference compound DL(±)AP7 against seizures induced by maximal electroshock (MES) were evaluated using mice.

For testing, electrodes were clipped to the ears of male CF-1 mice (20–25 g; Charles Rivers) and a current of 50 mA was delivered for 0.2 seconds to produce seizures. Drugs were dissolved in saline (0.9%; w/v) and administered fifteen minutes (ICV) or thirty minutes (IP) prior to testing. Injection protocols and group size were identicl to those described in example VI. Anticonvulsant activity was indicated by abolition of hindlimb extension such that hindlimb extension did not exceed a 90 degree angle with the plane of the body. Seizures were scored as being present or absent. Data was calculated as described in example VI.

Results are shown in Table 2. As expected, the reference compound DL(±)AP7 afforded dose-dependent protection against MES-induced seizures with calculated $ED_{50}$'s of 6.8 and 7.3 μg (ICU) and 127–170 mg/kg (IP) in two and three separate studies, respectively. Example IV proved to be moderately potent to attenuate MES-induced seizure activity following ICV administration (Table 2). However, example IV was approximately 11-fold less potent than DL(±)AP7 as an anticonvulsant in this test and 360-fold less potent as an anticonvulsant when compared to the activity of the example in the PTZ seizure model. Systemic (IP) administration of up to 350 mg/kg of example IV failed to prevent MES-induced seizures in any animal (Table 2; n=6).

The current results indicate example IV to be a potent anticonvulsant in the PTZseizure model; the relative lack of potency of example IV in the MES test suggests the compound possesses a novel spectrum of anticonvulsant selectivity relative to the reference compound, DL(±)AP7.

TABLE 2

POTENCY OF EXAMPLE IV AND DL(±)AP7 TO ANTAGONIZE PENTYLENTETRAZOL - AND MAXIMAL ELECTROSHOCK-INDUCED SEIZURES IN MALE CF-1 MICE

| COMPOUND | $ED_{50}$ icv (nmoles) | $ED_{50}$ icv (ug) | $ED_{50}$ ip (mmol/kg) | $ED_{50}$ ip (mg/kg) |
|---|---|---|---|---|
| PENTYLENETETRAZOL | | | | |
| EXAMPLE III* | 44 | 3.2 | | >350 |
| EXAMPLE IV* | 0.14; 0.19 | 0.04; 0.06 | 0.31; 0.47 | 90; 134 |
| $CL_{95}$ | 0.03–0.38 | 0.01–0.11 | 0.15–0.63 | 44–182 |
| $CL_{95}$ | 0.03–1.71 | 0.01–0.49 | 0.34–0.64 | 98–183 |
| DL(±)AP7* | 6.8 | 1.37 | 0.78–0.88 | 176–199 |
| $CL_{95}$ | 2–18 | 0.45–4.10 | N.D. | N.D. |
| MAXIMAL ELECTROSHOCK | | | | |
| EXAMPLE III | | >100 | | N.D. |
| EXAMPLE IV | 314 | 90 | >1.2 | >350 |
| $CL_{95}$ | 188–510 | 54–149 | N.D. | N.D. |
| DL(±)AP7* | 29;34 | 6.8;7.3 | 0.56–0.76 | 127–170 |
| $CL_{95}$ | 20–43 | 4.5–9.6 | N.D. | N.D. |
| $CL_{95}$ | 20–53 | 4.4–12 | N.D. | N.D. |

Method(s) have been described in the text. Where $ED_{50}$'s are shown, dose-reponse curves were generated using at least 5 concentrations of the indicated agent with 8 animals at each concentration. Values shown as ">" indicate the maximum dose tested and that none of the tested animals were protected from seizures.
*Where ninety-five percent confidence limits are not shown, the values represent the lowest and highest calculated $ED_{50}$ from at least three separate dose response curves each consisting of a minimum of five doses of DL(±)AP7 with eight animals tested at each dose. Where two separate values are shown for a single condition, each value represents the calculated $ED_{50}$ and ninety-five percent confidence intervals calculated from two separate dose-response curves generated on different occasions as described.
N.D. - not determined.

What is claimed is:

1. A potent selective excitatory amino acid neurotransmitter receptor antagonist having the general formula:

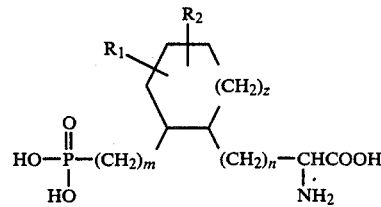

wherein $R_1$ and $R_2$ are the same or different and are selected from the group consisting of hydrogen, lower alkyl ($C_1$ to $C_6$), alkyl ($C_7$ to $C_{12}$), fatty acid chain ($C_{13}$ to $C_{24}$), aryl, aralkyl, hydroxyl, the stereoisomers being in their resolved or racemic form; n and m=1, 2, or 3 and z=0, 1 or 2; the cycloalkyl ring being replaced with the cycloalkenyl ring; and the pharmaceutically acceptable salts thereof.

2. The potent selective excitatory amino acid neurotransmitter receptor antagonist of claim 1 where $R_1$ and $R_2$ are both hydrogen and n=1, m=2 and z=1.

3. The compound according to claim 1 that is 3-{2-phosphonoethylcyclohexyl}-2-aminopropanoic acid.

4. The compound according to claim 1 that is 4-[2-phosphonomethylcyclohexyl]-2-aminobutanoic acid.

5. A pharmaceutical composition for relieving pain which comprises a pain relieving effective amount of one or more compounds of claim 1 with a pharmaceutically acceptable carrier and/or diluent.

6. A process of relieving pain in an animal in need thereof which comprises administering said compound of claim 1 or 5 parenterally, nasally, orally, rectally or a combination thereof to said animal in need thereof.

7. A pharmaceutical composition for treatment of convulsions or epilepsy which comprises an effective amount of one or more compounds of claim 1 with a pharmaceutically acceptable carrier and/or diluent.

8. A process for treating convulsions or epilepsy which comprises administering said compound of claim 1 or 7 parenterally, orally, nasally, rectally or a combination thereof to said animal in need thereof.

9. A pharmaceutical composition of enhancing cognition which comprises a cognition enhancing amount of one or more compounds of claim 1 with a pharmaceutically acceptable carrier and/or diluent.

10. A process of enhancing cognition which comprises administering said compound of claim 1 or 9 parenterally, orally, nasally, rectally or a combination thereof to said animal in need thereof.

11. A potent, selective excitatory amino acid neurotransmitter receptor antagonist having the general formula:

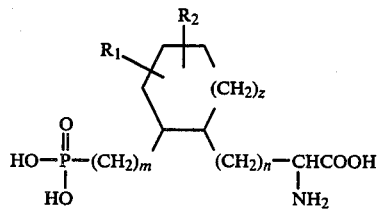

wherein $R_1$ and $R_2$ are the same or different and are selected from the group consisting of hydrogen, lower alkyl ($C_1$ to $C_6$), alkyl ($C_7$ to $C_{12}$), fatty acid chain ($C_{13}$ to $C_{24}$), aryl, aralkyl and hydroxyl; the stereoisomers being in their resolved or racemic form; n=1 and m=0, 1, 2 or 3; z=0, 1 or 2; and the pharmaceutically acceptable salts thereof.

12. The potent, selective excitatory amino acid neurotransmitter receptor antagonist of claim 11 wherein m=1, 2 or 3 and the sum of n+m is a number from 2 to 5.

13. The potent, selective excitatory amino acid neurotransmitter receptor antagonist of claim 12 wherein the sum of n+m is 3.

14. A potent, selective excitatory amino acid neurotransmitter receptor antagonist having the general formula:

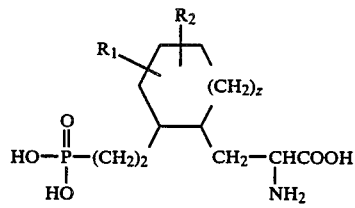

wherein $R_1$ and $R_2$ are the same or different and are selected from the group consisting of hydrogen, lower alkyl ($C_1$ to $C_6$), alkyl ($C_7$ to $C_{12}$), fatty acid chain ($C_{13}$ to $C_{24}$), aryl, aralkyl, hydroxyl; the stereoisomers being in their resolved or racemic form; z=0, 1 or 2; the cycloalkyl ring being replaced with the cycloalkenyl ring; and the pharmaceutically acceptable salts thereof.

15. A potent selective excitatory amino acid neurotransmitter receptor antagonist having the general formula:

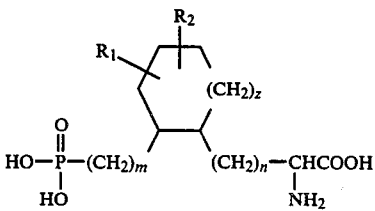

wherein $R_1$ and $R_2$ are the same or different and are selected from the group consisting of hydrogen, lower alkyl ($C_1$ to $C_6$), alkyl ($C_7$ to $C_{12}$), fatty acid chain ($C_{13}$ to $C_{24}$), aryl, aralkyl, hydroxyl, the stereoisomers being in their resolved or racemic form; n and m=1, 2, or 3 and z=0, 1 or 2; the cyclic ring is either a cycloalkanyl or a cycloalkenyl ring and the pharmaceutically acceptable salts thereof.

* * * * *